United States Patent [19]

Press

[11] 4,239,898

[45] Dec. 16, 1980

[54] NOVEL 4-(SUBSTITUTED-AMINOPHENOXY)-3-THIOPHENEMETHANOLS

[75] Inventor: Jeffery B. Press, Tuxedo, N.Y.

[73] Assignee: American Cyanamid Company, Stamford, Conn.

[21] Appl. No.: 120,198

[22] Filed: Feb. 11, 1980

[51] Int. Cl.$^3$ .................... C07D 333/16; A01K 31/38
[52] U.S. Cl. ........................................ 549/65; 424/275
[58] Field of Search ........................... 549/65; 260/571

[56] References Cited

U.S. PATENT DOCUMENTS 3,914,310  10/1975  Frick ..................................... 260/571

*Primary Examiner*—Alan Siegel
*Attorney, Agent, or Firm*—Edward A. Conroy, Jr.

[57] ABSTRACT

This disclosure describes novel 4-(substituted-aminophenoxy)-3-thiophenemethanols which are useful as anti-depressant agents.

4 Claims, No Drawings

NOVEL 4-(SUBSTITUTED-AMINOPHENOXY)-3-THIOPHENEMETHANOLS

DESCRIPTION OF THE INVENTION

This invention is concerned with certain novel 4-(substituted-aminophenoxy)-3-thiophenemethanol compounds that possess activity as anti-depressant agents. The present invention is concerned with the following specific compounds and the structural formulas thereof:

4-(o-methylaminophenoxy)-3-thiophenemethanol

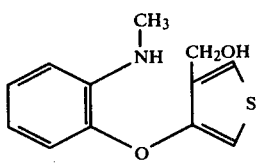

4-[2-(methylamino)-p-tolyloxy]-3-thiophenemethanol

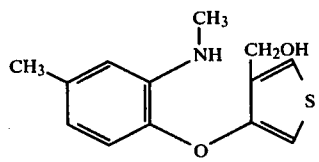

N-ethyl-6'-[4-(hydroxymethyl)-3-thienyloxy]-m-acetotoluidide

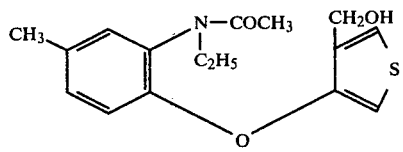

4-(2-dimethylamino-p-tolyloxy)-3-thiophenemethanol hydrochloride

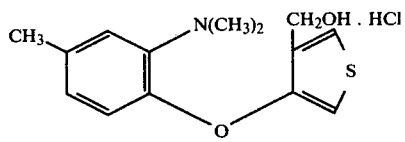

DETAILED DESCRIPTION OF THE INVENTION

The novel compounds of the present invention are obtainable as crystalline materials having characteristic melting points and absorption spectra. They are appreciably soluble in many organic solvents such as lower alkanols, acetone, ethyl acetate and the like but are generally insoluble in water.

The preparation of the novel compounds of the present invention are set forth in the following reaction schemes:

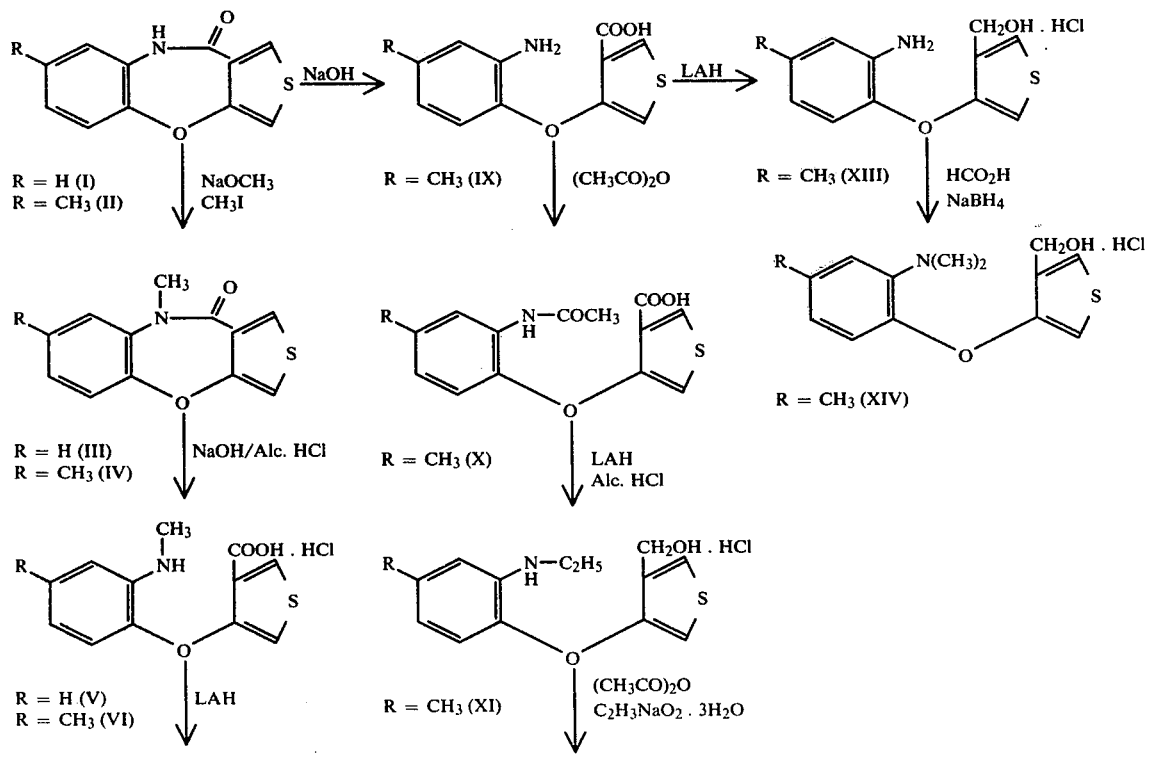

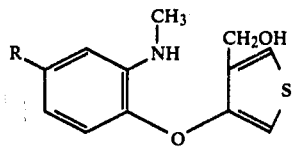

R = H (VII)
R = CH₃ (VIII)

-continued

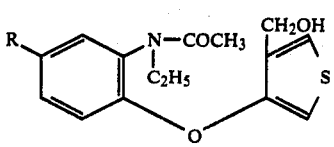

R = CH₃ (XII)

The starting material, thieno[3,4-b][1,5]benzoxazepin-10(9H)-one (I) or 7-methyl-thieno[3,4-b][1,5]benzoxazepin-10(9H)-one (II) in ethanol is treated with sodium methoxide and methyl iodide and extracted with methylene chloride to yield 9-methyl-thieno[3,4-b][1,5]benzoxazepin-10(9H)-one (III) and 7,9-dimethyl-thieno[3,4][1,5]benzoxazepin-10(9H)-one (IV) respectively. The above compounds III and IV are refluxed with 5 N sodium hydroxide for 16 hours, diluted with water, adjusted to pH 4–5 with hydrochloric acid and extracted with methylene chloride. The base compounds thus obtained are dissolved in ether and treated with alcoholic hydrochloric acid to give the corresponding 4-(o-methylaminophenoxy)-3-thiophenecarboxylic acid hydrochloride (V) and 4-(2-methylamino-p-tolyloxy)-3-thiophenecarboxylic acid hydrochloride (VI) compounds.

When compounds V and VI are refluxed with lithium aluminum hydride in ether for 16 hours, the products 4-(o-methylaminophenoxy)-3-thiophenemethanol (VII) and 4-[2-(methylamino)-p-tolyloxy]-3-thiophenemethanol (VIII) are respectively obtained.

When 7-methyl-thieno[3,4-b][1,5]benzoxazepin-10-(9H)-one is refluxed for 16 hours in 5 N sodium hydroxide, diluted with water, adjusted to pH 4–5 with dilute hydrochloric acid and extracted with methylene chloride, 4-(2-amino-p-tolyloxy)-3-thiophenecarboxylic acid (IX) is obtained. Compound IX is treated with acetic anhydride and extracted with ether to give 4-(2-acetamido-p-tolyloxy)-3-thiophenecarboxylic acid (X). When a stirred mixture of X and lithium aluminum hydride in ether is refluxed for 16 hours and the resulting product is dissolved in ether and treated with alcoholic hydrochloric acid, the compound 4-(2-ethylamino-p-tolyloxy)-3-thiophenemethanol hydrochloride (XI) is obtained.

When the hydrochloride (XI) in water is stirred with acetic anhydride and sodium acetate trihydrate is added, the product is collected and recrystallized from acetone-hexane to provide N-ethyl-6'-[4-(hydroxymethyl)-3-thienyloxy]-m-acetotoluidide (XII). When 4-(2-amino-p-tolyloxy)-3-thiophenecarboxylic acid (IX) and lithium aluminum hydride in ether is refluxed for 16 hours and the product is treated with alcoholic hydrochloric acid, 4-(2-amino-p-tolyloxy)-3-thiophenemethanol hydrochloride (XIII) is obtained.

Sodium borohydride pellets are added to a cooled solution (0°–10° C.) of XIII in formic acid and the mixture is stirred for 16 hours, poured onto ice and made basic with 10 N sodium hydroxide. The basic mixture is stirred for 30 minutes and extracted with methylene chloride. The organic solvent is evaporated in vacuo and the residue in ether is treated with alcoholic hydrochloric acid to provide 4-(2-dimethylamino-p-tolyloxy)-3-thiophenemethanol hydrochloride (XIV) as the product.

The compounds of the instant application have antidepressant activity as established by the inhibition of tetrabenazine induced depression of exploratory behavior in mice. In this test, doses of 25 mg./kg. of body weight of the test compounds are administered intraperitoneally or orally to groups of 5 mice one hour before the administration of tetrabenazine hexamate at an intraperitoneal dose of 30 mg./kg. of body weight which is known to depress markedly the exploratory behavior of normal mice. Thirty minutes later the mice are tested for their exploratory behavior. Individual mice are placed in the center of a horizontal disc (approximately 18 inches in diameter). Inhibition of the depression induced by tetrabenazine is considered present if the mice perform one or more of the following actions within 10 seconds after being placed on the disc:

(1) Animals move to the edge of the disc and look over the edge.
(2) Animals move 180° in place.
(3) Animals display a head movement of 90° immediately followed by a head movement in the opposite direction of at least 45°.

Administration of the test compounds to additional groups of 5 mice is repeated, the numbers of individual animals showing an anti-depressant response (normal exploratory behavior) is recorded and the results are analyzed by the following scheme:

| | No. Active/No. Tested | |
|---|---|---|
| 1st Stage (5 animals) | 0/5 | Reject (Ineffective Anti-depressant) |
| | 1/5–3/5 | Continue to Stage 2 |
| | ≧4/5 | Accept (Active Anti-depressant) |
| 2nd Stage | ≧4/10 | Accept |

This method has been described by Greenblatt, E. N. and Osterberg, A. C. in Toxicology and Applied Pharmacology, 7, 566–578 (1965). The results of this test, with the compounds of the present invention, are listed in Table I.

TABLE I

| Compound | Result |
|---|---|
| 4-(o-Methylaminophenoxy)-3-thiophenemethanol | Active |
| 4-[2-(Methylamino)-p-tolyloxy]-3-thiophenemethanol | Active |
| N-Ethyl-6'-[4-(hydroxymethyl)-3-thienyloxy]-m-acetotoluidide | Active |
| 4-(2-Dimethylamino-p-tolyloxy)-3-thiophenemethanol | Active |

The active components of this invention can be used in compositions such as tablets; the principal active ingredient is mixed with conventional tableting ingredients, such as corn starch, lactose, sucrose, sorbitol, talc, stearic acid, magnesium stearate, dicalcium phosphate, gums or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating.

The liquid forms in which the novel compositions of the present invention may be incorporated for administration include suitably flavored emulsions with edible oils, such as cottonseed oil, sesame oil, coconut oil, peanut oil, and the like, as well as sterile suspensions for parenteral use.

The term dosage form as described herein refers to physically discrete units suitable as unitary dosage for a warm-blooded animal subject, each unit containing a predetermined quantity of active component calculated to produce the desired therapeutic effect in association with the required pharmaceutical diluent carrier or vehicle. The dosage may vary from one to 70 mg./kg. of warm-blooded animal per day, preferably in multiple doses. The daily dosage requirement may be from 50 to 2000 mg. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The invention will be described in greater detail in conjunction with the following specific examples.

EXAMPLE 1

4-(o-Methylaminophenoxy)-3-thiophenemethanol

To a stirred suspension of 10.0 g. of thieno[3,4-b][1,5]benzoxazepin-10(9H)-one (prepared as described in Example 1 of U.S. Pat. No. 4,144,235) in 100 ml. of ethanol is added 10.0 g. of sodium methoxide and after 30 minutes 100 ml. of methyl iodide is added. After stirring for one additional hour, the reaction mixture is diluted with water and extracted with methylene chloride. The product is collected with the aid of hexane to give 8.5 g. of 9-methylthieno[3,4-b][1,5]benzoxazepin-10(9H)-one as a white solid, m.p. 128°–130° C.

An 8.0 g. amount of the preceding compound in 400 ml. of 5 N sodium hydroxide is heated under reflux for 16 hours. The resulting solution is cooled and an oil is separated which is dissolved upon the addition of 100 ml. of water. The solution is stirred and adjusted to pH 4–5 by the addition of concentrated hydrochloric acid. The product is extracted in methylene chloride. The solvent is evaporated in vacuo to give 8.0 g. of 4-(o-methylaminophenoxy)-3-thiophenecarboxylic acid. A 2.0 g. amount of this product is dissolved in 25 ml. of ether and treated with 2.5 N alcoholic hydrochloric acid to provide 1.75 g. of 4-(o-methylaminophenoxy)-3-thiophenecarboxylic acid hydrochloride as white crystals, m.p. 208°–210° C.

A stirred mixture of 4.0 g. of the above hydrochloride and 4.0 g. of lithium aluminum hydride in 200 ml. of ether is heated under reflux for 16 hours. Then water is added dropwise to the reaction mixture to decompose the excess lithium aluminum hydride. The ether layer is decanted, dried and evaporated. The residue is treated with hexane to give 3.4 g. of the product of the Example as a cream colored solid, m.p. 69°–70° C.

EXAMPLE 2

4-[2-(Methylamino)-p-tolyloxy]-3-thiophenemethanol

To a stirred suspension of 20.0 g. of 7-methyl-thieno[3,4-b][1,5]benzoxazepin-10(9H)-one (prepared as described in Example 7 of U.S. Pat. No. 4,144,235) in 200 ml. of ethanol is added 20.0 g. of sodium methoxide and, after 30 minutes, 200 ml. of methyl iodide is added. After stirred for one additional hour, the reaction mixture is diluted with water and extracted with methylene chloride. The product is collected with the aid of hexane to give 17.3 g. of 7,9-dimethyl-thieno[3,4-b][1,5]benzoxazepin-10-(9H)-one.

A 17.3 g. amount of the preceding compound in one liter of 5 N sodium hydroxide is heated under reflux for 16 hours. The resulting solution is cooled and an oil is separated which is dissolved upon the addition of 200 ml. of water. The solution is stirred and adjusted to pH 4–5 by the addition of concentrated hydrochloric acid. The solution is extracted in methylene chloride and the solvent is evaporated in vacuo to yield a gum. The gum is dissolved in 500 ml. of ether and an excess of alcoholic hydrochloric acid is added dropwise to separate the product which is collected by filtration to give 18.0 g. of 4-(2-methylamino-p-tolyloxy)-3-thiophenecarboxylic acid hydrochloride. The product is recrystallized from ethanol:ether to give white crystals, m.p. 216°–217° C.

A 13.5 g. amount of the above compound and 13.5 g. of lithium aluminum hydride in 675 ml. of ether is heated under reflux with stirring for 16 hours. The procedure of Example 1 is continued to give 10.5 g. of the product of the Example as white crystals; m.p. 134°–135° C.

EXAMPLE 3

N-Ethyl-6'-[4-(hydroxymethyl)-3-thienyloxy]-m-acetotoluidide

A 10.0 g. amount of 7-methyl-thieno[3,4-b][1,5]-benzoxazepin-10(9H)-one (prepared as described in Example 7 of U.S. Pat. No. 4,144,235) in 500 ml. of 5 N sodium hydroxide is heated under reflux for 16 hours. The solution is cooled with separation of an oil. The oil is dissolved on the addition of water and the solution is adjusted to pH 4–5 with 5% aqueous hydrochloric acid. The solution is extracted with methylene chloride. The organic solvent is evaporated to give 8.0 g. of 4-(2-amino-p-tolyloxy)-3-thiophenecarboxylic acid as a white solid, m.p. 154°–155° C.

A 21.0 ml. amount of acetic anhydride is added to 7.0 g. of the above compound with swirling. Solution takes place followed by separation of a product. After 10 minutes ether is added, the product is collected and washed with ether to give 6.2 g. of 4-(2-acetamido-p-tolyloxy)-3-thiophenecarboxylic acid as white crystals, m.p. 194°–195° C.

A stirred mixture of 4.0 g. of the preceding compound and 4.0 g. of lithium aluminum hydride in 200 ml. of ether is heated under reflux for 16 hours. Then water is added dropwise to the reaction mixture is decompose the excess lithium aluminum hydride. The ether layer is decanted, dried and evaporated to give the compound 4-(2-ethylamino-p-tolyloxy)-3-thiophenemethanol. The compound is dissolved in 40 ml. of ether and treated with a slight excess of alcoholic hydrochloric acid to give 3.0 g. of 4-(2-ethylamino-p-tolyloxy)-3-thiophenemethanol hydrochloride as white crystals, m.p. 135° C.

A 1.5 ml. amount of acetic anhydride is added to a solution of 1.5 g. of the above hydrochloride compound in 15 ml. of water with stirring. Then 1.5 g. of sodium acetate trihydrate is added and a product is separated. The crude product is collected, washed with water and dried. The product of the Example is recrystallized from acetone:hexane to yield 1.25 g. of white crystals, m.p. 128°–129° C.

EXAMPLE 4

4-(2-Dimethylamino-p-tolyloxy-3-thiophenemethanol, hydrochloride

A stirred mixture of 5.0 g. of 4-(2-amino-p-tolyloxy)-3-thiophenecarboxylic acid and 5.0 g. of lithium aluminum hydride in 250 ml. of ether is heated under reflux for 16 hours. Then water is added dropwise to the reaction mixture to decompose the excess lithium aluminum hydride. The ether layer is decanted, dried and evaporated to give a gum. The gum, in 50 ml. of ether, is treated with a slight excess of 2.6 N alcoholic hydrochloric acid which is added dropwise with stirring. The resulting product is collected by filtration, washed with ether and dried to yield 4.5 g. of 4-(2-amino-p-tolyloxy)-3-thiophenemethanol, hydrochloride as white crystals, m.p. 133°–135° C.

To a 1.0 g. amount of the preceding compound in 30 ml. of formic acid (>95%), cooled to 0°–10° C., is added one-at-a-time with intermittent cooling 10 pellets of sodium borohydride. The mixture is stirred for 16 hours at room temperature and is then poured onto ice and made strongly basic with 10 N sodium hydroxide. The basic mixture is stirred for 30 minutes, then extracted with methylene chloride. The organic solvent is evaporated to yield 4-(2-dimethylamino-p-tolyloxy)-3-thiophenemethanol as a gum. The gum is dissolved in 50 ml. of ether and treated with a slight excess of alcoholic hydrochloric acid added dropwise with stirring. The gum which separates is crystallized on scratching and is collected. The product is recrystallized from acetone-hexane to give 550 mg. of the desired product as white crystals, m.p. 134°–136° C.

We claim:
1. The compound 4-(o-methylaminophenoxy)-3-thiophenemethanol.
2. The compound 4-[2-(methlamino)-p-tolyloxy]-3-thiophenemethanol.
3. The compound N-ethyl-6'-[4-(hydroxymethyl)-3-thienyloxy]-m-acetotoluidide.
4. The compound 4-(2-dimethylamino-p-tolyloxy)-3-thiophenemethanol hydrochloride.

* * * * *